United States Patent
Lin et al.

(10) Patent No.: US 9,008,394 B2
(45) Date of Patent: Apr. 14, 2015

(54) METHODS AND APPARATUS FOR DETERMINING BRAIN CORTICAL THICKNESS

(75) Inventors: Zhongmin Steve Lin, New Berlin, WI (US); Gopal Avinash, Menomonee Falls, WI (US); Saad Sirohey, Pewaukee, WI (US); Ananth Mohan, Waukesha, WI (US); Satoshi Minoshima, Seattle, WA (US)

(73) Assignees: General Electric Company, Schenectady, NY (US); University of Washington, Seattle, WA (US)

( * ) Notice: Subject to any disclaimer, the term of this patent is extended or adjusted under 35 U.S.C. 154(b) by 1104 days.

(21) Appl. No.: 12/324,498

(22) Filed: Nov. 26, 2008

(65) Prior Publication Data

US 2010/0130848 A1    May 27, 2010

(51) Int. Cl.
*A61B 5/055* (2006.01)
*A61B 5/107* (2006.01)

(52) U.S. Cl.
CPC ............... *A61B 5/1075* (2013.01); *A61B 5/055* (2013.01); *G06T 2207/10088* (2013.01); *G06T 2207/30016* (2013.01)

(58) Field of Classification Search
CPC .. A61B 5/055; A61B 5/1075; G01R 33/5608; G06T 2207/10088; G06T 2207/30016
USPC ......... 600/407, 410, 411, 484, 529, 544, 547; 382/128, 130, 131
See application file for complete search history.

(56) References Cited

U.S. PATENT DOCUMENTS

| | | | |
|---|---|---|---|
| 4,976,267 A | 12/1990 | Jeffcott et al. | |
| 5,331,970 A | 7/1994 | Gevins et al. | |
| 6,411,729 B1 | 6/2002 | Grunkin | |
| 6,591,004 B1 * | 7/2003 | VanEssen et al. | 382/154 |
| 6,744,911 B1 | 6/2004 | Avila et al. | |
| 7,155,042 B1 * | 12/2006 | Cowan et al. | 382/128 |
| 7,215,994 B2 * | 5/2007 | Huiku | 600/544 |
| 7,635,337 B2 * | 12/2009 | Huiku et al. | 600/484 |
| 2003/0176780 A1 | 9/2003 | Arnold et al. | |
| 2004/0114789 A1 * | 6/2004 | Saha et al. | 382/128 |
| 2005/0084146 A1 * | 4/2005 | Watson et al. | 382/131 |
| 2006/0241374 A1 * | 10/2006 | George et al. | 600/410 |
| 2009/0024021 A1 | 1/2009 | George et al. | |
| 2010/0080432 A1 * | 4/2010 | Lilja et al. | 382/131 |

* cited by examiner

*Primary Examiner* — Baisakhi Roy
(74) *Attorney, Agent, or Firm* — Dean Small; The Small Patent Law Group, LLC

(57) ABSTRACT

Methods and apparatus for determining brain cortical thickness are provided. One method includes determining an intensity profile at each of a plurality of cortical surface points of an imaged brain using brain tissue image data and calculating a cortical thickness based on a parametrically determined transition point of each intensity profile.

18 Claims, 8 Drawing Sheets

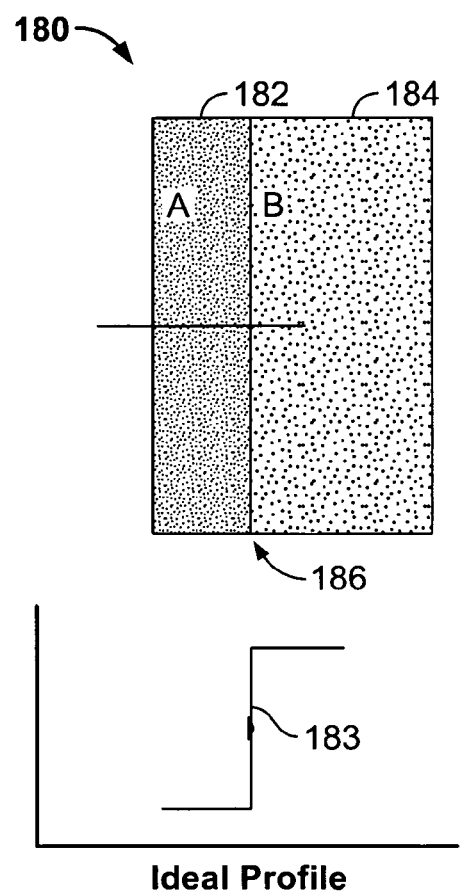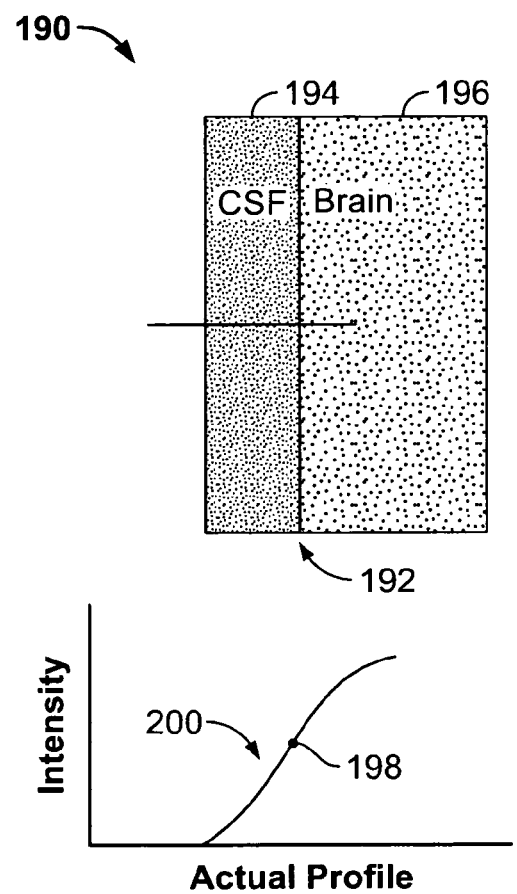
FIG. 8
FIG. 9

METHODS AND APPARATUS FOR DETERMINING BRAIN CORTICAL THICKNESS

BACKGROUND OF THE INVENTION

This invention relates generally to diagnostic imaging systems, and more particularly to systems and methods for determining a cortical thickness of an imaged brain using image data from a diagnostic imaging system.

Diagnostic imaging systems are used in many different applications. For example, magnetic resonance (MR) imaging systems may be used to image the structure and function of the human body. MR imaging of the brain has been used to evaluate different regions of the brain to determine pathological changes, which have been associated with different brain diseases such as Alzheimer's Disease, Parkinson's Disease, etc. These diseases often cannot be determined by confidence with standardized laboratory tests.

With respect to Alzheimer's Disease, for example, a change in the thickness of the cerebral cortex, which plays an important role in the memory and behavioral process of the brain has been used to identify the disease. The human cortex is a highly folded layer of neurons referred to as gray matter. Gray matter is a thin layer that covers the cerebrum. White matter supports the cerebral gray matter and connects various gray matter areas. Because of limited image resolution and partial volume effects when imaging the brain, the image intensities vary continuously from cerebral spinal fluid to gray matter and then to white matter. Accordingly, there is no clear boundary between white and gray matter in MR images, which is used to measure the thickness of the cortex.

Conventional methods used to measure the thickness of the cortex employ automatic segmentation processes to distinguish gray and white matters. These conventional methods are based on preset criteria to separate gray and white matter, which may result in less than satisfactory results. Using manual segmentation has similar problems, for example, image window leveling affects the identification of the gray and white matter boundary. These conventional segmentation methods are also complicated, resulting in a processor intensive and time consuming process. For example, to segment out the very complex thin layer of the cortex, active contour methods are known that rely mainly on gradient features for the segmentation of gray matter from an image and deformable models to segment the three-dimensional (3D) surface. However, not only are these methods computationally intense and time intensive, but the results of the gray matter segmentation are often not reliable or robust. In particular, the intensities of the brain gray matter overlap quite a lot with the intensities of the brain white matter. Also, the 3D structure of the brain is very complicated, especially on the gray and white matter interfaces. Additionally, limited spatial resolution and partial volume effects of the MR make it difficult to accurately find the pial surface and the interface between gray and white matters. Therefore, conventional methods are not robust or statistically well founded, resulting in problems with repeatability and comparison of results.

BRIEF DESCRIPTION OF THE INVENTION

In accordance with one embodiment, a method for calculating cortical thickness from image data using at least one processor is provided. The method includes determining an intensity profile at each of a plurality of cortical surface points of an imaged brain using brain tissue image data and calculating a cortical thickness based on a parametrically determined transition point of each intensity profile.

In accordance with another embodiment, a method for calculating cortical thickness from image data using at least one processor is provided. The method includes creating a one-dimensional profile through each of a plurality of surface points of a three-dimensional imaged brain. The one-dimensional profiles are perpendicular to a surface of the three-dimensional imaged brain at each of the surface points. The method further includes generating a cortical thickness map on each of the surface points based on a cortical thickness calculated from each of the one-dimensional profiles.

In accordance with yet another embodiment, a diagnostic imaging system is provided that includes an imaging portion configured to acquire images of a human head. The diagnostic imaging system also includes a processing portion configured to determine an intensity profile at each of a plurality of surface points of an imaged brain using brain tissue image data corresponding to the images of the human head and calculate a cortical thickness based on a parametrically determined transition point of each intensity profile.

BRIEF DESCRIPTION OF THE DRAWINGS

FIG. 8 is a graph illustrating an ideal intensity profile.

FIG. 9 is a graph illustrating an exemplary actual intensity profile.

DETAILED DESCRIPTION OF THE INVENTION

Figure 1:
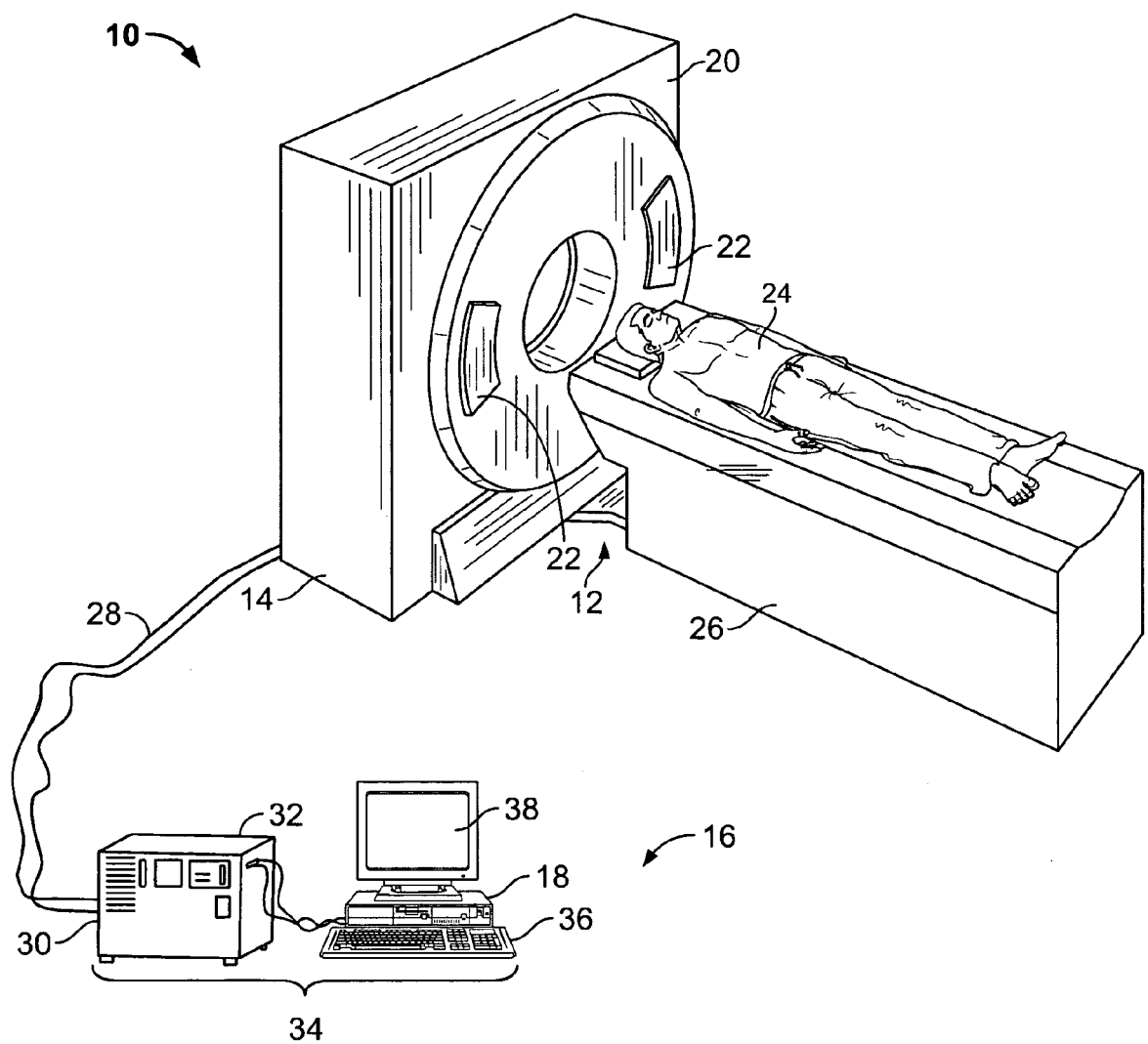
FIG. 1 is a pictorial view of an imaging system formed in accordance with various embodiments of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

Various embodiments of the invention provide methods and systems for determining cortical thickness from image data, such as Magnetic Resonance (MR) images. The various embodiments use one-dimensional profiles at a plurality of surface points of a three-dimensional imaged brain to calculate cortical thickness. The cortical thickness calculations are based on parametrically determined transition points of each intensity profile.

Various embodiments of the invention provide an imaging system 10 as shown in FIG. 1. It should be appreciated that although the imaging system 10 is illustrated as a single modality imaging system, the various embodiments of the invention may be implemented in or with multi-modality imaging systems. The imaging system 10 may be any type imaging system, for example, different types of medical imaging systems, such as a Magnetic Resonance Imaging (MRI), Computed Tomography (CT), Positron Emission Tomography (PET), a Single Photon Emission Computed Tomography (SPECT), as well as an ultrasound system, or any other system capable of generating images, particularly images of a head or brain. Moreover, the various embodiments are not limited to medical imaging systems for imaging human subjects, but may include veterinary or non-medical systems for imaging non-human objects, etc.

Referring to FIG. 1, the imaging system 10 includes an imaging portion 12 that includes an imaging unit 14 (e.g., imaging scanner) and a processing portion 16 that may include a processor 18 or other computing or controller device. In particular, the imaging unit 14 enables the imaging system 10 to scan an object or patient 24 to acquire image data, which may be image data of all or a portion of the object or patient 24. The imaging unit 14 includes a gantry 20 that includes one or more imaging components 22 (two are shown) that allow acquisition of the image data. The one or more imaging components 22 may be for example, one or more magnets for magnetic resonance imaging, an x-ray source and detector for computed-tomography imaging, or gamma cameras for nuclear medicine imaging. The imaging components 22 produce signals that represent image data that is communicated to the processing portion 16 via a communication link 28 that may be wired or wireless. It should be noted that the signals may be configured in different protocols, etc. It should also be noted that during an imaging scan by the imaging unit 14, the gantry 20 and the imaging components 22 mounted thereon or therein may rotate about a center of rotation or may remain stationary. The patient 24 may be positioned within the gantry 20 using, for example, a motorized table 26.

Thus, in operation an output of one or more of the imaging components 22 is transmitted to the processing portion 16, and vice versa, which for example, may include, transmitting signals to or from the processor 18 through a control interface 30. The processor 18 also may generate control signals for controlling the position of the motorized table 26 or the gantry 20 (and imaging components 22) based on, for example, user inputs or a predetermined scan. During a scan, image data, magnetic resonance image data from the imaging components 22 may be communicated to the processor 18 through a data interface 32 via the control interface 30. The processor 18 and associated hardware and software used to acquire and process data may be collectively referred to as a workstation 34. The workstation 34 includes a keyboard 36 and/or other input devices such as a mouse, a pointer, and the like, and a monitor 38. The monitor 38 displays image data and may accept input from a user if a touchscreen is available. The processor 18 also may be configured to calculate a cortical thickness based on acquired image data as described in more detail herein.

Figure 2:
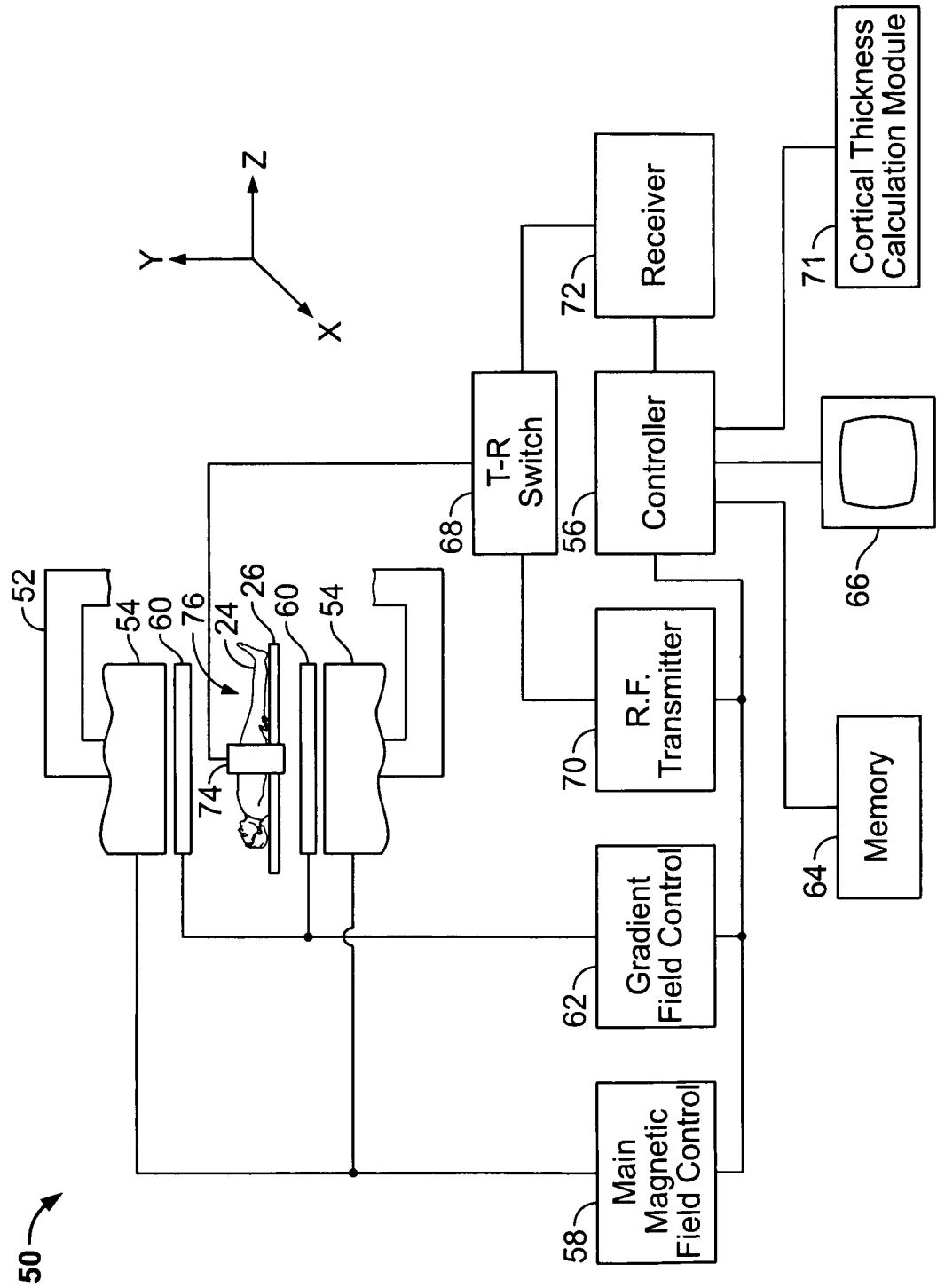
FIG. 2 is a block diagram of a magnetic resonance imaging system formed in accordance with various embodiments of the invention.

For illustrative purposes only, various embodiments of the invention may be implemented to determine a cortical thickness from an MRI system 50 as shown in FIG. 2. In particular, the MRI system 50 includes an electromagnet 52, pole pieces 54, a controller 56, a main magnetic field control 58, a gradient coil sub-system 60, a gradient field control 62, a memory 64, a display device 66, a transmit-receive (T-R) switch 68, a radio frequency (RF) transmitter 70, a receiver 72 and an array of detectors 74 (e.g., a cylindrical array of equally-spaced detectors). It should be noted that although electromagnet 52 is a C-shaped magnet, other shapes of electromagnets can be used.

In operation, a body of an object, such as a patient 24 or a phantom to be imaged, is placed in an opening or gap 76 between pole pieces 54 on a suitable support, for example, motorized table 26 or other patient table. The electromagnet 52 produces a uniform and static main magnetic field $B_o$ across the gap 76. The strength of the electromagnetic field in the gap 76 and correspondingly in the patient 24, is controlled by the controller 56 via the main magnetic field control 58, which also controls a supply of energizing current to the electromagnet 52.

The gradient coil sub-system 60, having one or more gradient coils, is provided so that a magnetic gradient can be imposed on the magnetic field $B_o$ in the gap 74 between pole pieces 54 in any one or more of three orthogonal directions x, y, and z. Gradient coil sub-system 60 is energized by gradient field control 62 and is also controlled by the controller 56.

The array 74, which may include a plurality of coils (e.g., resonant surface coils), is arranged to simultaneously detect MR signals from the patient 24. The array 74 is selectably interconnected to one of the RF transmitter 70 or receiver 72 by the T-R switch 68. The RF transmitter 70 and T-R switch 68 are controlled by the controller 56 such that RF field pulses or signals are generated by the RF transmitter 70 and selectively applied to the patient 24 for excitation of magnetic resonance in the patient 24. While the RF excitation pulses are being applied to the patient 24, the T-R switch 68 is also actuated to decouple the receiver 72 from the array 74.

Following application of the RF pulses, the T-R switch 68 is again actuated to decouple the array 74 from the RF transmitter 70 and to couple the array 74 to the receiver 72. The array 74 includes detectors that operate to detect or sense the MR signals resulting from the excited nuclei in the patient 24 and communicates the MR signals to the receiver 72. These detected MR signals are in turn communicated to the controller 56. The controller 56 includes a processor (e.g., image reconstruction processor), for example, the processor 18, that controls the processing of the MR signals to produce signals representative of an image of the patient 24. A cortical thickness calculation module 71 also may be provided in communication with the controller 56 (or as part of the controller 56, for example, part of the processor 18), to calculate a cortical thickness based on MR images of a brain as described in more detail herein.

The processed signals representative of the image are also transmitted to the display device 66 to provide a visual display of the image. Specifically, the MR signals fill or form a k-space that is Fourier transformed to obtain a viewable image. The processed signals representative of the image are then transmitted to the display device 66.

In operation, the magnetic field $B_o$ generated by the electromagnet 52 is applied to the patient 24 that lies along a z-axis of a Cartesian coordinate system, the origin of which is within the patient 24. The uniform magnetic field Bo being applied has the effect of aligning nuclear spins, a quantum mechanical property of nuclei within the patient 24, along the y-axis. In response to the RF pulses of a proper resonant frequency being generated by the RF transmitter 70, and that are orientated within an x-z plane perpendicular to the y-axis, the nuclei resonate at their Larmor frequencies. In a typical imaging sequence, an RF pulse centered about the Larmor frequency is applied to the patient 24 at the same time a magnetic field gradient Gz is being applied along the z-axis by means of the gradient coil sub-system 60. The gradient Gz causes nuclei in a slice with a limited width through the patient 24 along the x-y plane, to have a resonant frequency and to be excited into resonance.

After excitation of the nuclei in the slice, magnetic field gradients Gx and Gy are applied along the x and y axes respectively. The magnetic field gradient Gx along the x-axis causes the nuclei to precess at different frequencies depending on the position of the nuclei along the x-axis. Essentially, Gx spatially encodes the precessing nuclei by frequency, referred to as frequency encoding. A y-axis gradient Gy is incremented through a series of values and encodes a y-axis rate of change of phase of the precessing nuclei as a function of the amplitude of the gradient Gy, a process referred to as phase encoding.

Variations and modifications are contemplated. For example, the array 74 may be replaced with coil arrays. Further, and for example, instead of the electromagnet 52, a super-conducting magnet configured having a cylindrical bore shape may be used as part of an open MRI system having a vertical $B_o$ field.

It should again be noted that the various embodiments of the present invention are not limited to use in connection with the MRI system 50 described herein, but may be implemented in connection with any type of system capable of acquiring images, particularly diagnostic images of a head or brain.

Figure 3:
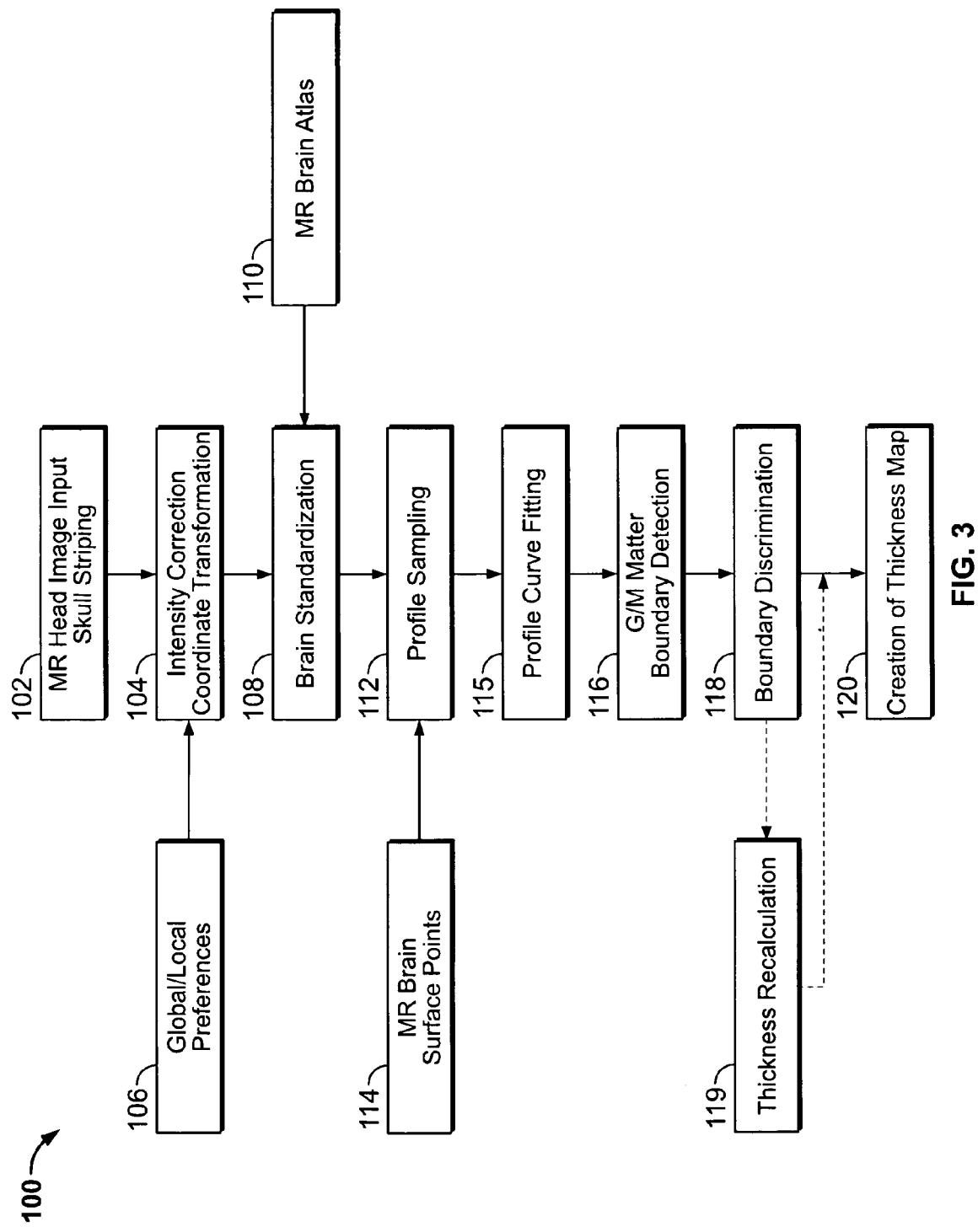
FIG. 3 is flowchart of a method for determining cortical thickness in accordance with various embodiments of the invention.

Various embodiments of the invention provide a method 100, as shown in FIG. 3, for determining cortical thickness from image data. It should be noted that although the method 100 is described in connection with MR images of the brain, different types of images (e.g., CT images) or combined images (e.g., PET/MRI images) may be used. At least one technical effect of the various embodiments is to determine a cortical thickness based on an intensity profile at each of a plurality of cortical surface points of an imaged brain. The various embodiments convert the thickness calculation process from calculations in three-dimensions to calculations in one-dimension. Further, the determination of the cortical thickness may be based on a plurality of different mathematical parameters. Thus, the various embodiments employ a statistical approach to describe the local intensity variations from cerebrospinal fluid (CSF) to brain white matter and to analyze intensity profiles to determine the gray/white matter boundary and calculate cortical thickness. A less computationally intensive and faster process for determining cortical thickness is provided. Using a refined profile sample and curve fitting, the stability of the cortical thickness calculation may be increased. Moreover, the cortical thickness calculation based on local profiles is less immune to MR intensity non-uniformity and partial volume effects.

Specifically, image data, for example, MR head image data is obtained at 102 and a skull stripping process performed. For example, high-resolution T1-weighted MR brain images may be used, which images in one embodiment have a one millimeter (mm) resolution. In particular, the MR head data is preprocessed to extract a brain tissue image using any known process. For example, known skull stripping, registration and masking processes may be used to remove image pixels corresponding to the imaged skull such that brain tissue pixels remain. Accordingly, pixels corresponding to the cranium are removed from the image data. It should be noted that some image editing also may be performed.

The method 100 also includes further data preprocessing wherein intensity correction and coordinate transformation may be performed at 104. For example, as is known, non-uniformities in pixel intensity across the brain tissue data may be corrected using conventional MR image processing to provide a consistent profile analysis as described in more detail below. For example, a gradient weighted smoothing process may be performed. Further coordinate transformation may be performed. In particular, the MR image data corresponding to the brain tissue is transformed into the same coordinate space as the coordinate space for an MR atlas that will be used for brain standardization as described below. For example, in one embodiment, the MR image data may be re-sampled to the same image matrix as that of the MR atlas. When performing the intensity correction and coordinate transformation, global or local preferences may be applied at 106. For example, preprocessing parameters may be applied to all portions of the image or to only specific portions of the image.

After the MR brain tissue image data has been preprocessed including transforming the data into the coordinate space of the MR atlas, brain standardization is performed at 108 using a brain atlas at 110. For example, a patient MR brain standardization as is known may be performed, which essentially provides a geometric standardization. In particular, the brain tissue image may be elastically registered to the MR atlas. For example, a standard MR brain atlas is created at 110 and used for the patient MR brain standardization. This MR brain standardization includes identifying the Anterior and Posterior Commisures (AC-PC) and other anatomy landmarkers defined in the brain atlas for use in brain registration. For example, using the brain atlas, the location of brain structures may be identified independent from the individual size and overall shape of an imaged brain.

It should be noted that wherein reference is made herein to a brain atlas, this generally refers to a common representation of brain and serves as a reference system to which other brain scans can be mapped. For example, two different brain atlases that may be used are the Talairach atlas and Montreal Neurological Institute (MNI) atlas.

Thus, by using, for example, the Talairach atlas, the Talairach coordinate system may defined by making two points, in particular, the AC and PC, which lie on a straight horizontal line. Because these two points lie on the midsagittal plane, the coordinate system is completely defined by requiring this plane to be vertical. Thereafter, distances in the Talairach coordinates are measured from the AC as the origin. It should be noted that Talairach coordinates are sometimes referred to as stereotaxic coordinates. By defining standard anatomical landmarks that can be identified on different patient's imaged brains (the AC and PC), the MR image data for a particular patient can be transformed into the brain standard space, for example, a standard Talairach space. Thus, the brain tissue data extracted from the MR data is standardized by mapping the brain tissue data to a predefined atlas space.

Thereafter, intensity profiles normal to the surface are created, and in particular, profile sampling is performed at 112 to generate intensity profiles at each of a plurality of cortical surface points of the standardized imaged brain tissue. The cortical surface points are MR brain surface points that are defined at 114. It should be noted that where reference is made herein to brain or cortical surface points, this refers generally to reference points that in various embodiments are located outside, but very close to the brain atlas surface. Brain surface points in some embodiments are manually defined (e.g., by a user input with a mouse) and verified. The surface points in various embodiments are mostly in the CSF.

Figures 4, 5:
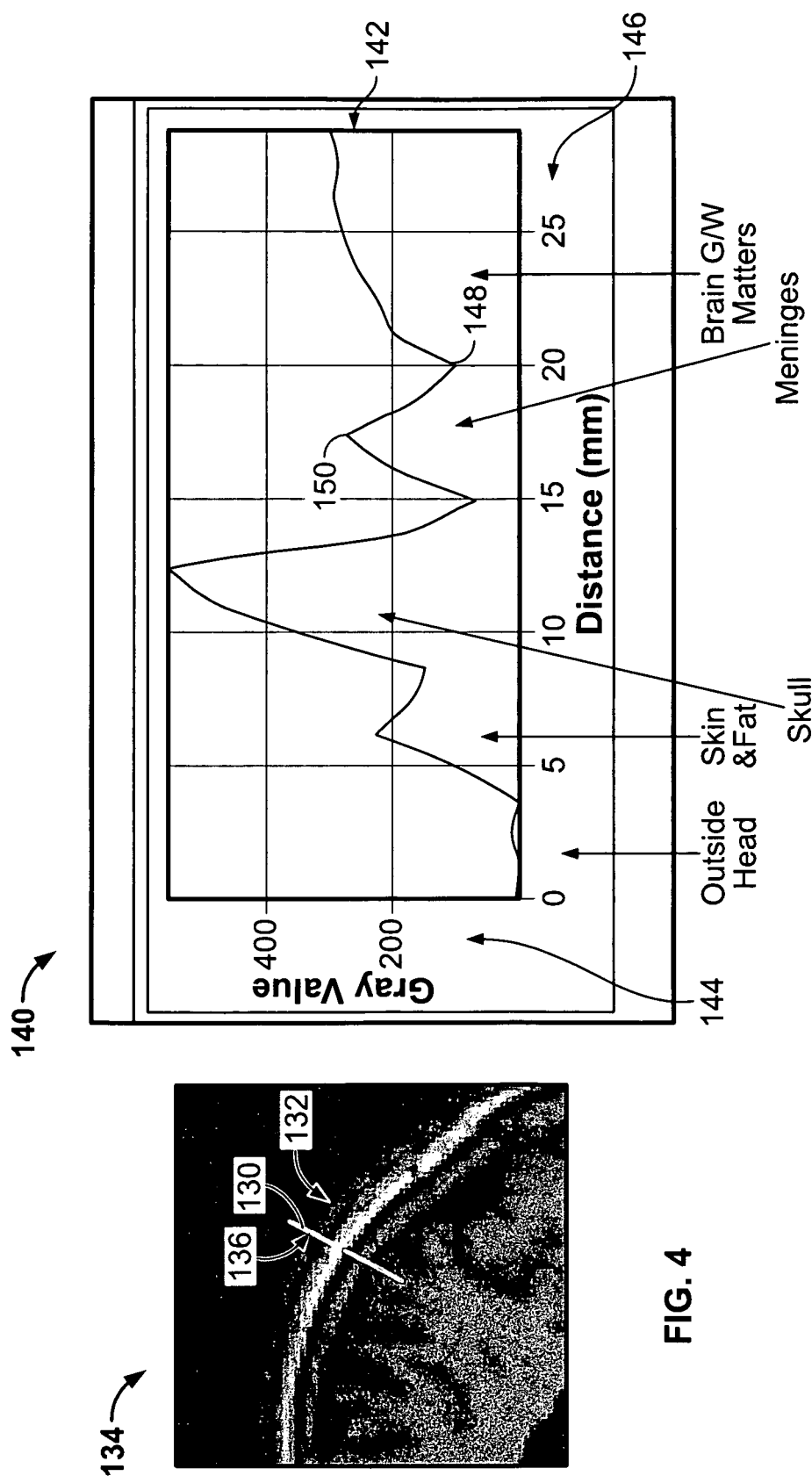
FIG. 4 is a graph of an intensity profile corresponding to a surface point of an imaged head.
FIG. 5 is an image of a skull illustrating a one-dimensional surface profile generated in accordance with various embodiments of the invention corresponding to the intensity profile of FIG. 4.

Specifically, and with respect to creating intensity profiles at 112, in various embodiments of the invention, a plurality of pre-defined brain surface points (e.g., 16,000 brain surface points) distributed over the brain surface are identified. For each surface point, a direction that is perpendicular to the brain surface is then determined. Thereafter, at each surface point, an intensity profile that is perpendicular to the brain surface is created as shown in FIGS. 4 and 5. Specifically, as shown in FIG. 4, intensity profiles are created, namely one-dimensional intensity profiles 130 (only a single profile 130 is illustrated for simplicity) are created that are perpendicular to a surface 132 of a three-dimensional imaged brain 134 at a plurality of points 136 (only one point 136 is shown for simplicity). Thus, as shown in FIG. 4, a typical profile is generated from a one-dimensional profile formed from a point outside the imaged brain 134 and passing through the skin, skull, meninges, gray matter and finally stopping in the white matter. In some embodiments, the surface point is located at the meninges or CSF. It should be noted that to reduce the profile noise, each point on the profile may be interpolated from neighboring points (e.g., eight neighboring or adjacent points). It further should be noted that the profile steps may be calculated at arbitrary intervals by oversampling points along the profile.

An exemplary intensity profile 140 (illustrated as a graph 142) corresponding to the one-dimensional intensity profile 130 is shown in the FIG. 5. In the graph 142, the vertical axis 144 corresponds to grayscale values and the horizontal axis 146 corresponds to distance from the surface point 136 (shown in FIG. 4). It should be noted that each of the peaks in the graph 142 correspond to different layers of the imaged brain 134 (shown in FIG. 4)

It also should be noted that the MR intensity outside the pial surface (surface immediately investing the brain and spinal cord) is usually quite low and can be used to search for the start point of the meninges/CSF to white matter profiles. In various embodiments, the complete length of the intensity profile 140 that is used in the searching for the profile between the meninges/CSF and white matter is about fifteen mm.

Figures 6, 7:
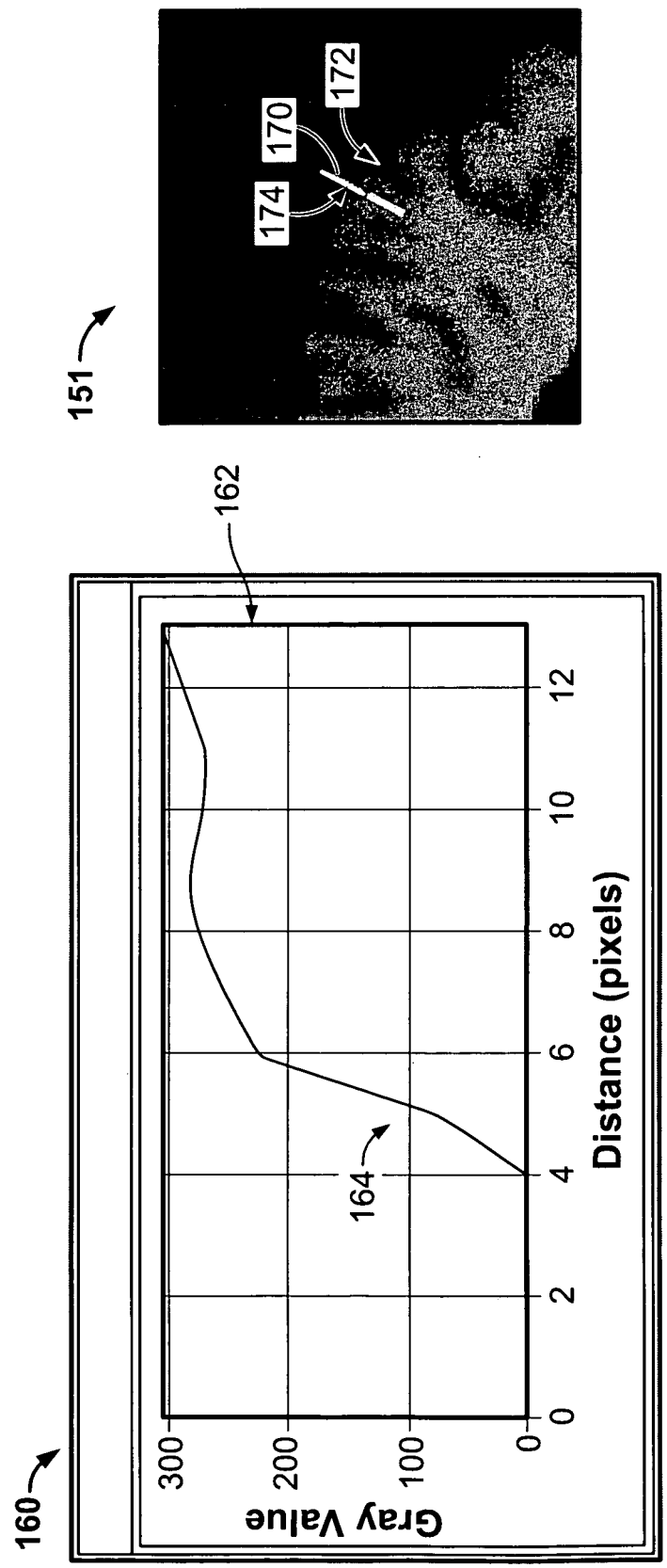
FIG. 6 is a graph of an intensity profile corresponding to a surface point of an imaged head with skull stripping.
FIG. 7 is an image of brain tissue illustrating a one-dimensional intensity profile generated in accordance with various embodiments of the invention corresponding to the intensity profile of FIG. 6.

Additionally, a point 148, which is the valley in the graph 142 following a peak 150 identifying the meninges, is where the intensity profile 140 enters the brain tissue, which may be removed by skull stripping as described herein. Thus, an exemplary intensity profile 160 (illustrated as a graph 162) from the meninges/CSF to the white matter of a segmented brain is shown in FIG. 6, which corresponds to the one-dimensional intensity profiles 170 shown in FIG. 7 that is perpendicular to a surface 172 of a three-dimensional imaged brain 151 at a point 174, which now illustrates only the brain tissue (i.e., a standardized brain tissue MR image with skull stripping).

Referring again to the method 100 of FIG. 3, after the intensity profiles from the one-dimensional intensity profiles are generated at 112, a cortical thickness is parametrically determined, for example, using a profile curve fitting at 115 on the curve 164 (shown in FIG. 6) and the border between gray matter and white matter is detected at 116. It should be noted that although the illustrated parametrical determination is based on a curve fitting process, any mathematical parameter or other parametrical determination may be used. Moreover, the method 100 may determine an inflection point of the intensity profile 160 or maximum and minimum values may be used to as described in more detail herein.

In particular, both gray and white matters are part of brain. It should be noted that the MR intensity of the gray matter is slightly less than the MR intensity of white matter. However, the MR intensities of the gray and white matters overlap. It further should be noted that anatomically, gray matter is a thin layer (usually less than five mm) outside the white matter. The gray and white matters, thus, blend with each other. For example, an ideal intensity profile 180 of two materials 182 and 184 in a junction area 186 is illustrated FIG. 8. The intensity profile 180 is a step function for this ideal situation as illustrated by the curve 183. However, because image resolution and the densities of the brain gray/white matters are varied continuously, the actual intensity profile 190 of the border 192 between the CSF 194 and the brain 196 (identified by the point 198 on the curve 200) as shown in FIG. 9 is not a step function, but can be modeled by a Sigmoid or other similar function as described herein. This model can then be used to analyze the MR intensity profile from CSF to the white matter as described in more detail herein.

Figure 10:
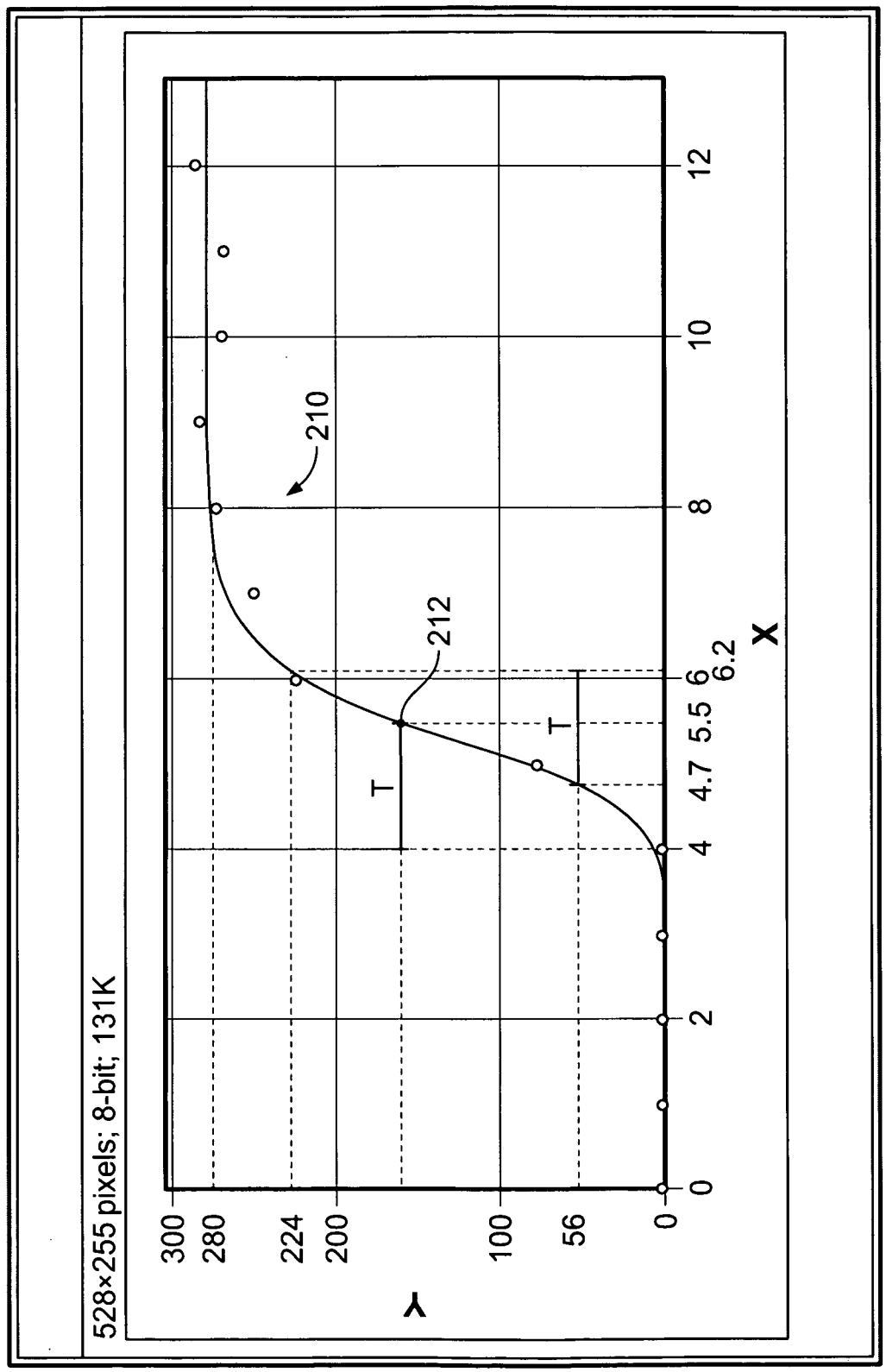
FIG. 10 is a graph of a curve fit to an intensity profile in accordance with various embodiments of the invention.

Thus, as shown in FIG. 10, the MR intensity profile 160 is fit to a Rodbard curve 210, which is then used to determine the boundary of the gray and white matters at 118 in the method 100 of FIG. 3 (i.e., boundary discrimination). For example, the boundary may be identified as the inflection point 212 of the curve 210. It should be noted that any other criteria for the boundary selection can be used. For example, a point corresponding to a preset percentage distance from the highest intensity value (white matter) to the lowest intensity value (gray matter) may be selected as the boundary. In general, the various embodiments may use the same parameter or criteria such that consistent boundary selection is provided that results in clinically relevant gray and white matter boundary segmentation. Thus, if the same parameters or criteria are used between different scans of the same brain, a relative change may be determined. It should be noted that the vertical axis corresponds to height value and the horizontal axis corresponds to a number of pixels (or distance) in FIG. 10.

Local cortical thickness for each of the intensity profiles, for example, the intensity profiles 160 are then determined using the curve fits to create a thickness map at 120. For example, as shown in FIG. 10, a cortical thickness T may be determined based on the distance from the inflection point 212 to a minimum value of the curve 210 (that may be greater than zero). For example, as illustrated, the distance from the inflection point 212 of the curve 210 at about 150 to a minimum value point (of about 10) of the curve 210 is 5.5 minus 4, which equals a cortical thickness of 1.5.

Figure 11:
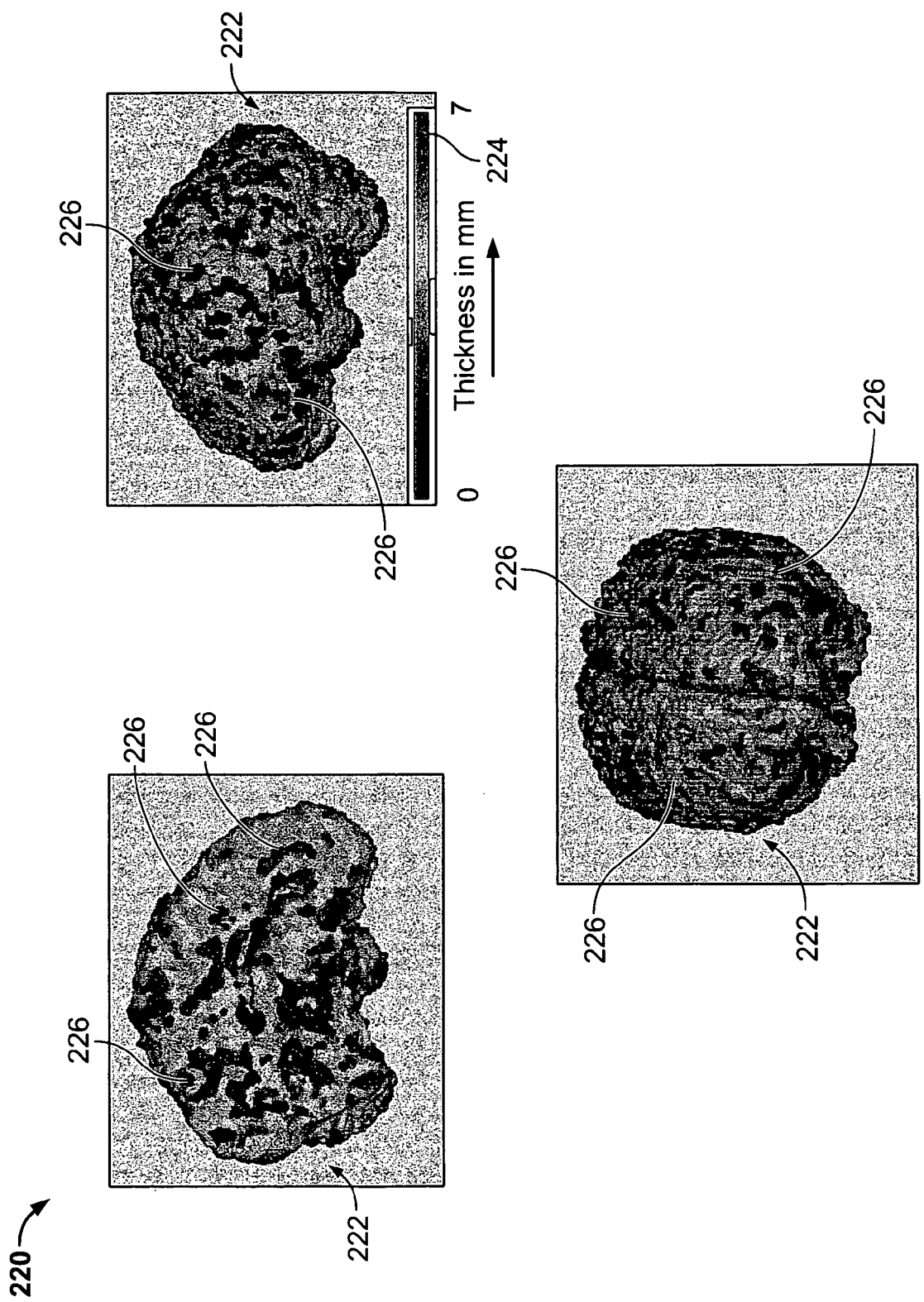
FIG. 11 are images corresponding to a cortical thickness map formed in accordance with various embodiments of the invention.

As another example, the cortical thickness T may be determined based on the distance from a maximum value to a minimum value of the curve 210, wherein the maximum and minimum values may be a predetermined level (or, for example, a percentage distance from a maximum or minimum value). Accordingly, for the curve 210, the height of the curve is about 280. Thus, using a minimum value that is twenty percent of 280, which equals about 56 and having a corresponding pixel value of about 4.7 and using a maximum value that is eighty percent of 280, which equals about 224 and having a corresponding pixel value of about 6.2, the cortical thickness (T) can be calculated as 6.2 minus 4.7, which equals 1.5. A cortical thickness (T) can be calculated for each intensity profile and then a cortical thickness map 220 as shown in FIG. 11 may be created for each of the intensity profiles corresponding to a surface point of the imaged brain 222. It should be noted that three different views of the imaged brain 222 are shown for the intensity map 220. However, the imaged brain 222 may be rotated or oriented in different positions, for example, by a user. The imaged brain is color coded, which color coding may indicate a cortical thickness for different surface points 226 as defined by a color code key 224 (defining a range of cortical thickness), where different colors represent different cortical thicknesses.

Moreover, because of, for example, poor registration, poor segmentation or improper surface points, some intensity profiles are not suitable for the calculation of the cortical thickness. In theses instances, the calculated results may be beyond the true/actual or reliable values. For example, the method 100 may process the calculated cortical thicknesses results to determine if any thickness value exceeds a thickness threshold, for example, which in some embodiments is an upper limit of about six mm. Cortical thicknesses exceeding the thickness threshold may be eliminated or disregarded, or the cortical thicknesses corresponding to adjacent surface points may be interpolated to replace the cortical thickness value exceeding the thickness threshold.

In some embodiments, surface points with cortical thicknesses exceeding the thickness threshold may be recalculated at 119. In particular, several points (e.g., ten points) that are in the brain and closest to the surface point are selected. The corresponding intensity profiles that pass through these points and perpendicular to the brain surface are created. Each of the intensity profiles is then fitted to a model to calculate a cortical thickness value. Cortical thickness values are also subjected to a criterion (e.g., minimum, median) to determine an effective thickness value that is then projected onto the surface point.

Thus, various embodiments of the invention extract intensity profiles perpendicular to surface locations of an imaged brain. A cortical thickness is then parametrically determined for each of the intensity profiles at each of the surface locations. A cortical thickness map then may be generated.

Some embodiments of the present invention provide a machine-readable medium or media having instructions recorded thereon for a processor or computer to operate an imaging apparatus to perform one or more embodiments of the methods described herein. The medium or media may be any type of CD-ROM, DVD, floppy disk, hard disk, optical disk, flash RAM drive, or other type of computer-readable medium or a combination thereof.

The various embodiments and/or components, for example, the processors, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for calculating cortical thickness from image data using at least one processor, the method comprising:
    determining an intensity profile of brain tissue at each of a plurality of cortical surface points of an imaged brain using brain tissue image data, the intensity profile passing through a plurality of different matter within the brain tissue;
    fitting a curve to the intensity profile;
    parametrically determining a transition point of the intensity profile by determining an inflection point of the intensity profile; and
    calculating a cortical thickness based on the parametrically determined transition point of the intensity profile.

2. A method in accordance with claim 1 wherein the fitting comprises a Sigmoid fit.

3. A method in accordance with claim 1 wherein the plurality of surface points comprises predefined surface locations.

4. A method in accordance with claim 3 further comprising determining the predefined surface locations based on a predefined atlas space.

5. A method in accordance with claim 1 wherein the intensity profiles are perpendicular to the cortical surface at each of the cortical surface points.

6. A method in accordance with claim 1 further comprising determining intensity profiles for surface points having a value that exceeds a cortical thickness threshold.

7. A method in accordance with claim 6 further comprising adjusting the calculated cortical thickness based on the surface points having a value that exceeds the cortical thickness threshold.

8. A method in accordance with claim 7 wherein the adjusting comprises one of disregarding the intensity profile for the surface points having a value that exceeds the cortical thickness threshold and interpolating the calculated cortical thickness from adjacent surface points.

9. A method in accordance with claim 1 wherein the brain tissue image data comprises magnetic resonance data.

10. A method in accordance with claim 1 further comprising creating a thickness map based on the calculated cortical thicknesses.

11. A in method in accordance with claim 1, wherein the cortical thickness is calculated based on a predetermined minimum value of the curve.

12. A method in accordance with claim 1, wherein the cortical thickness is calculated based on a predetermined range disposed about the inflection point.

13. A method for calculating cortical thickness from image data using at least one processor, the method comprising:
    creating a one-dimensional profile of brain tissue through a plurality of surface points of a three-dimensional imaged brain, wherein the plurality of surface points comprises predefined surface locations based on a predefined atlas space, the one-dimensional profiles perpendicular to a surface of the three-dimensional imaged brain at the surface points and passing through a plurality of different matter within the brain tissue; and
    generating a cortical thickness map on the surface points based on a cortical thickness calculated from the one-dimensional profiles, wherein generating the cortical thickness map comprises determining a transition point of the one-dimensional profiles and using the transition points of the one-dimensional profiles to calculate the cortical thickness.

14. A method in accordance with claim 13 further comprising using a statistical parameter to determine a transition point along the one-dimensional profiles to identify a cortical boundary.

15. A method in accordance with claim 13 further comprising defining a maximum point and a minimum point of the one-dimensional intensity profiles to calculate the cortical thickness.

16. A method in accordance with claim 13 wherein the three-dimensional imaged brain is formed from magnetic resonance images.

17. A diagnostic imaging system comprising:
    an imaging portion configured to acquire images of a human head; and
    a processing portion configured to determine an intensity profile of brain tissue at each of a plurality of surface points of an imaged brain using brain tissue image data corresponding to the images of the human head, the intensity profile passing through a plurality of different matter within the brain tissue, the processing portion further configured to perform a curve fitting to parametrically determine a transition point of the intensity profile and calculate a cortical thickness based on the parametrically determined transition point of the intensity profile.

18. A diagnostic imaging system in accordance with claim 17 wherein the brain tissue image data comprises magnetic resonance image data.

* * * * *